ively selected from hydrogens, alkyls and al-
United States Patent

Bunes

[11] 4,249,007
[45] Feb. 3, 1981

[54] ANTHRAQUINONE COLORANTS

[75] Inventor: Leonard A. Bunes, San Carlos, Calif.

[73] Assignee: Dynapol, Palo Alto, Calif.

[21] Appl. No.: 35,163

[22] Filed: May 2, 1979

Related U.S. Application Data

[62] Division of Ser. No. 751,857, Dec. 17, 1976, Pat. No. 4,182,885.

[51] Int. Cl.³ .......................................... C07D 221/18
[52] U.S. Cl. ...................................................... 546/58
[58] Field of Search .......................................... 546/58

[56] References Cited

FOREIGN PATENT DOCUMENTS 658114 3/1938 Fed. Rep. of Germany .
827961 2/1938 France .
964602 7/1964 United Kingdom .
965235 7/1964 United Kingdom .

Primary Examiner—Jose Tovar
Assistant Examiner—D. B. Springer
Attorney, Agent, or Firm—William H. Benz

[57] ABSTRACT

Red colors having the anthraquinone structure

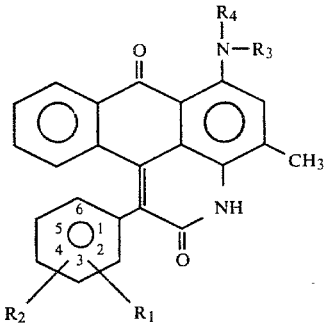

are disclosed wherein $R_1$ and $R_2$ are independently selected from among hydrogen, halos, lower alkyls, lower alkoxies, nitros, and sulfonates, and $R_3$ and $R_4$ are independently selected from hydrogens, alkyls and alkylsulfonates. Precursors are disclosed as well. In a preferred embodiment $R_4$ is an alkyl-containing polymer linking a plurality of anthraquinones into a polymeric colorant especially useful as a nonabsorbable colorant for edibles.

11 Claims, No Drawings

ANTHRAQUINONE COLORANTS

This is a division application Ser. No. 751,857, filed Dec. 17, 1976 and now U.S. Pat. No. 4,182,885.

BACKGROUND OF THE INVENTION

1. Field of the Invention

This invention relates to colorants. More particularly, it concerns a family of red colorants which find special application as red colorants for edibles.

2. The Prior Art

FD&C Red #2, a monoazo dye of the formula

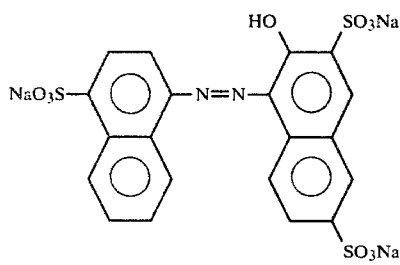

commonly known as Amaranth, was among the most widely used colors in foods, drugs and cosmetics. In 1975 these uses were prohibited in the United States when the Food and Drug Administration ruled that the dye's safety was questionable. The removal from commerce of this compound has left a great need. Edibles such as cherry, raspberry, and strawberry-flavored gelatin desserts, candies and jams, and nonedibles such as inks and dyes were formulated around the particular tint and hue of this color. Several replacement colors have been proposed but have not been fully acceptable. For example, FD&C Red #40, another monoazo dye which has the formula

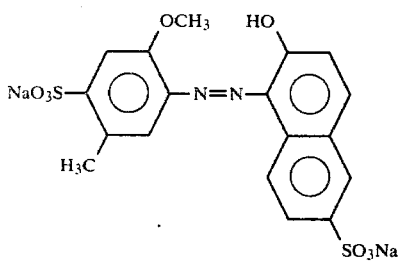

and which is disclosed in U.S. Pat. No. 3,640,733, issued Feb. 8, 1972 to Rast et al., is now being used as a replacement. This material has a brownish cast which interferes with many uses. Natural colors, such as are extracted from beets, have been suggested as well but have low coloring power, and thus unacceptably high costs in use. The present invention seeks to provide a replacement for now-delisted azo color Red #2. This invention discloses a limited family of new anthraquinone colorants which are excellent color matches for Red #2. The colorants of this invention can take on two forms. They can be monomeric, as have been all food colors approved for use heretofore. Preferably, however, these new colors are in polymeric form. As is disclosed in U.S. Pat. No. 3,920,855, issued Nov. 18, 1975 to Dawson et al., in copending United States patent application Ser. No. 520,530, filed November 4, 1975 by Gless et al., and now U.S. Pat. No. 4,018,826 and in Japanese Patent Applications of Tanabe, such as Nos. 41-14433, 41-14434 and 44-13382, having colors in polymeric form can be advantageous. When polymeric colors are used in edibles, if the size of the molecules of polymeric color exceeds a certain limit—usually a molecular size of from about 1000 to 2000 Daltons—and if the color compounds do not break down and thus maintain this size, the polymeric colors are not absorbed through the walls of the gastrointestinal tract. This means that when such materials are eaten, they essentially pass directly through the gastrointestinal tract. They are not taken into the body or its systemic circulation and thus any risk of possible systemic toxicity is eliminated.

STATEMENT OF THE INVENTION

The new and useful anthraquinone colors of this invention have the following structural formula

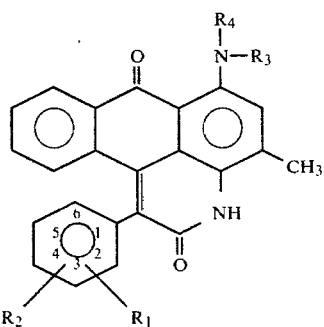

wherein $R_1$ and $R_2$ are independently selected from hydrogen, halos of atomic number 9 through 53, nitros, lower alkyls and lower alkoxies of from 1 to 3 carbon atoms, and sulfonates; and $R_3$ and $R_4$ are independently selected from hydrogens, lower alkyls and alkyl sulfonates of from 1 to 4 carbon atoms and a noncrosslinked organic polymeric backbone which covalently links together a plurality of units of this color into polymeric form.

DETAILED DESCRIPTION OF THIS INVENTION

The colors of this invention may be in monomeric or polymeric form. In monomeric form they have the structural formula wherein $R_1$ and $R_2$ independently are selected from the class of substituents consisting of hydrogen; halos selected from fluoro, chloro, bromo and iodo; nitro; lower alkoxies selected from methoxy, ethoxy or propoxy;

lower alkyls selected from methyl, ethyl and propyl and sulfonate.

The remaining three positions on the pendant non-fused aromatic ring to which $R_1$ and $R_2$ are covalently bonded carry hydrogens. $R_1$ and $R_2$ preferably are separately attached to the ring at the 2, 4 or 6 positions. Preferably, $R_1$ is hydrogen and $R_2$ is selected from the class of substituents set forth hereinabove. More preferably, $R_1$ is hydrogen and $R_2$ is hydrogen, chloro or methoxy.

In a most preferred color $R_1$ and $R_2$ are both hydrogen. This is an excellent red. Surprisingly, the presence of the diverse range of other $R_1$ and $R_2$ substituents, varying from strongly electron withdrawing nitro groups to strongly electron donating alkoxy groups makes only minor differences in the shade of these colors. A group of preferred colors having a single nonhydrogen substituent on the nonfused ring is shown in Table I.

TABLE I

| Substituent | Ring Position |
|---|---|
| Cl | 2 or 4 |
| Br | 2 or 4 |
| $SO_3^- M^+$ | 4 |
| $NO_2$ | 2 or 4 |
| $-O-CH_3$ | 2 or 4 |
| $-OC_2H_5$ | 2 or 4 |

In monomeric form, the colors of this invention have $R_3$ and $R_4$ independently selected from hydrogen, lower alkyls of from 1 to 4 carbons, i.e., methyl, ethyl, propyl or butyl, and lower alkyl sulfonates of from 1 to 4 carbon atoms, i.e., methyl sulfonate, ethyl sulfonate, propyl sulfonate and butyl sulfonate. In preferred monomeric colors $R_3$ is hydrogen and $R_4$ is hydrogen or a 1 to 4 carbon alkyl or alkyl sulfonate.

The colors of this invention preferably are in polymeric form. This can be represented structurally by defining $R_4$ as a polymer linking together a plurality of units of the color molecule or and this is considered to be a better description, the polymeric colors can be represented by the following structural formula:

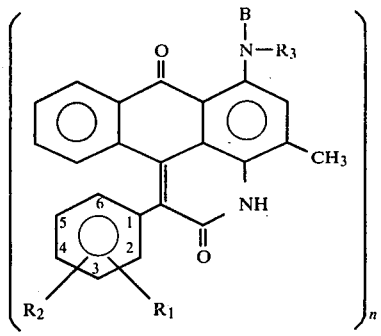

wherein $R_1$, $R_2$ and $R_3$ are as previously defined not only in general but also as to preferences. B is an organic polymeric backbone attached to N by a covalent bond and characterized by having essentially no cross-links and by containing only covalent bonds which are stable under the acidic, basic, and enzymatic conditions of the mammalian gastrointestinal tract; n is a number greater than 1, preferably from 10 to 2000 and more preferably from 20 to 1000.

Preferred backbones are carbon-oxygen ether backbones and essentially linear alkyl carbon-carbon backbones containing pendant primary and lower alkyl secondary amines in acetylated or unacetylated form, with or without additional covalently attached pendant groups such as sulfonates, phosphonates, carboxyls and the like. Examples of these preferred backbones and the resulting polymeric colors are given in Table II.

TABLE II

| Backbone | Polymeric Color |
|---|---|
| polyvinylamine | $+CH-CH_2\!\!\frac{}{n}+CH-CH_2\!\frac{}{m}$<br>$\quad\mid \qquad\qquad\quad \mid$<br>$\quad NH \qquad\qquad NH_2$<br>$\quad\mid$<br>$\quad Chrom.*$<br>n = 10 to 4000, preferably 100–2000<br>m = 0.3 to 5n |
| polyvinylamine with acetylayted residual amines | $+CH-CH_2\!\!\frac{}{n}+CH-CH_2\!\frac{}{m}$<br>$\quad\mid \qquad\qquad\quad \mid$<br>$\quad NH \qquad\qquad NHAc$<br>$\quad\mid$<br>$\quad Chrom.$ |
| copoly(vinylamine/ vinylsulfonate) (shown in sodium form) (other alkaline metals will work) (amine can be 1 to 3 carbon N-alkyl amine as well) | $+CH-CH_2\!\!\frac{}{n}+CH-CH_2\!\frac{}{p}+CH-CH_2\!\frac{}{m}$<br>$\quad\mid \qquad\qquad\quad \mid \qquad\qquad\qquad \mid$<br>$\quad NH \qquad\qquad SO_3^- \;^+Na \qquad NH_2$<br>$\quad\mid$<br>$\quad Chrom.$<br>n = 10 to 2000<br>m = 0.3 to 5n<br>p = 0.3 to 2 (n + m) |
| copoly(vinylamine/vinyl sulfonate) with acetylated residual amines. | $+CH-CH_2\!\!\frac{}{n}+CH-CH_2\!\frac{}{p}+CH-CH_2\!\frac{}{m}$<br>$\quad\mid \qquad\qquad\quad \mid \qquad\qquad\qquad \mid$<br>$\quad NH \qquad\qquad SO_3^- \;^+Na \qquad NHAc$<br>$\quad\mid$<br>$\quad Chrom.$ |
| poly N-methylvinylamine (other n-lower alkyl amines can be used as well) | $-CH-CH_2)_n(CH-CH_2\!\frac{}{m}$<br>$\quad\mid \qquad\qquad\quad \mid$<br>$\quad N-CH_3 \qquad\quad N-CH_3$<br>$\quad\mid \qquad\qquad\qquad \mid$<br>$\quad Chrom. \qquad\qquad H$ |

TABLE II-continued

| Backbone | Polymeric Color |
|---|---|
| copoly(vinylamine/ acrylic acid) (amines can be acetylated as well) | $\text{+CH-CH}_2\text{)}_n\text{(CH-CH}_2\text{)}_m\text{(CH-CH}_2\text{)}_p$<br>  \|               \|              \|<br>  NH           NH$_2$        COOH<br>  \|<br>  Chrom. |
| sulfonated polyvinylamine or N-methylvinylamine or the like R = lower alkyl of 1 to 3 carbons or hydrogen (secondary alkyl and primary amines can be acetylated) | $\text{+CH-CH}_2\text{)}_n\text{(CH-CH}_2\text{)}_m\text{CH-CH}_2\text{)}_p$<br>  \|               \|              \|<br>  NR           NR           NR<br>  \|               \|              \|<br>  Chrom.        H            SO$_3^-$ Na$^+$ |
| aminated poly(epichloro- hydrin) (with added sulfamates | $\text{+CH-CH}_2\text{-O)}_n\text{(CH-CH}_2\text{-O)}_m\text{(CH-CH}_2\text{-O)}_p$<br>  \|               \|              \|<br>  NH           NH$_2$        NH<br>  \|                              \|<br>  Chrom.                       SO$_3^-$ $^+$Na |
| aminated and acetylated poly(epichlorohydrin) | $\text{+CH-CH}_2\text{-O)}_n\text{(CH-CH}_2\text{-O)}_m$<br>  \|               \|<br>  NH           NHAc<br>  \|<br>  Chrom. |

*Chrom. equals

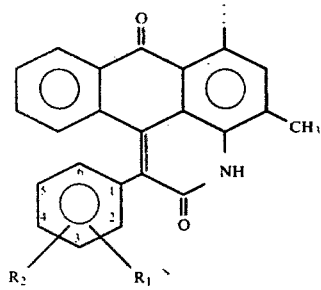

Among backbones, polyvinylamine and copoly(-vinylamine/vinylsulfonate), either acetylated or un-acetylated, are preferred. These preferred backbones preferably have molecular weights of about 10,000 to about 150,000 Daltons and, in the case of the copolymer, an amine to sulfonate ratio of from 1:1 to 3:1. A polyvinylamine meeting this weight range has from about 200 to about 3000 units, a copolymer—from about 60 to about 1800 amine units. The choice among backbones often depends upon the degree of water solubility required of the final polymer colorant product. Polar groups such as carboxyls, phosphonates and especially sulfonates are required in the polymeric colorant to impart good water solubility properties. When the color unit itself contains sulfonates, i.e., when $R_1$ and/or $R_2$ are sulfonates or alkyl sulfonates, it is not necessary to have these polar groups attached to the backbone as well. When the color unit does not contain sulfonate $R_1$'s or $R_2$'s, good water solubilities, i.e., solubility in pH 7 room temperature water of at least 1000 ppm, are achieved only when a backbone containing polar groups—such as the copolymer backbones—is employed.

The colors of this invention may be prepared by the following two routes. These routes are presented as exemplary methods and are not to be construed as limiting the scope of this invention.

The first route begins with 1-amino-2-methyl-4-bromoanthraquinone, a material marketed by Sandoz Color and Chemical under the tradename AMBAX, or made as in Example I.

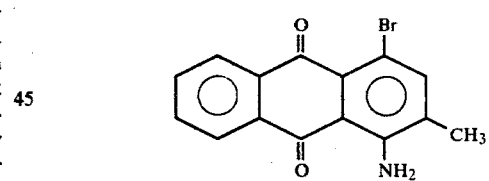

This material is reacted with a benzylic acid chloride,

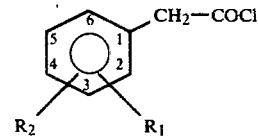

corresponding to the nonfused pendant aromatic ring desired in the colorant as follows:

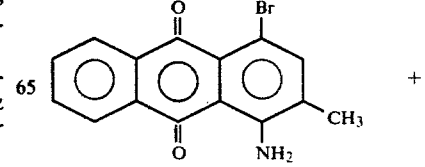

+

-continued

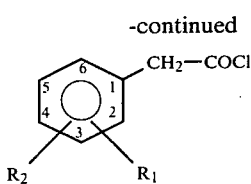

→

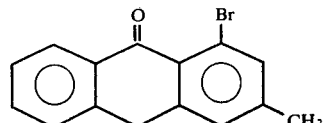

This reaction is carried out in liquid phase in a reaction solvent. Suitable solvents include aprotic organic liquids especially cyclic and acyclic olefinically saturated aromatic or aliphatic hydrocarbons such as benzene, toluene, xylene, hexane, cyclohexane, heptane, $C_6$–$C_9$ hydrocarbon mixed solvents, cyclic and acyclic ethers such as dimethoxyethane, 1,4-dioxane, diglyme, and the like. This reaction is carried out at elevated temperatures such as from 50° C. to 150° C. with temperatures of from 75° C. to 130° C. being preferred. In our work the atmospheric reflux temperature of the solvent has been used. The reaction could be carried out under pressure to obtain higher temperatures if desired. Reaction time is inversely proportional to temperature. Reaction times of from a few (3–5) minutes to about 24 hours generally are employed. The following examples will aid in selecting times and temperatures. At 50°–80° C., times of about 10–24 hours are usually adequate. At 110°–115° C., the reaction appears complete in about 20–30 minutes with times of from 20 minutes to three hours being used; at 150° C., 3 to 5 minutes are adequate. Generally, a slight molar excess of the acid halide is employed since it is the less expensive reactant. AMBAX/acid halide ratios of 1:1 to 1:2.0 are generally preferred with ratio of 1:1.1 to 1:1.3 being most preferred.

This AMBAX addition product is then cyclized with base.

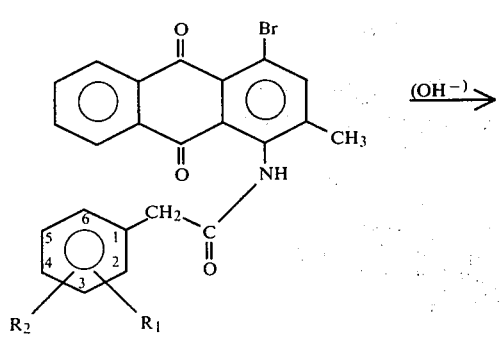

-continued

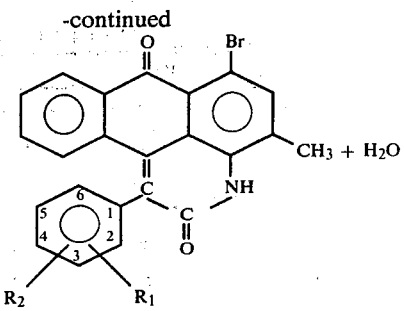

The base employed is not critical, any strong inorganic base such as NaOH, KOH or the like will work. From 0.5 to 2 equivalents (basic colorant) of base may be used. This step is generally carried out at elevated temperatures such as 90° C. to 250° C. with temperatures of 90° C. to 200° C. being preferred. This step can immediately follow the acid halide addition step by adding base to the crude halide addition product and heating for from about five minutes to about 24 hours. At 80° C. 24 hours is a good reaction time, at 110°–120° C., 15 minutes to one hour are employed. At 175°–200° C., five minutes are employed. Otherwise, the halide addition product can be isolated by evaporation of solvent and crystallization and dissolved in fresh inert aprotic solvent such as those used for the addition and then treated with base. This more complicated method offers some yield advantages. Both methods yield the new intermediate

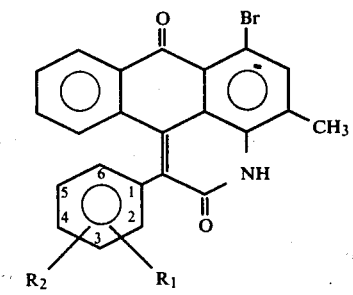

wherein $R_1$ and $R_2$ are as already defined. It will be appreciated that the Br substituent is present principally because the AMBAX starting material is a bromo compound. Other halo leaving groups (i.e., $Cl^-$, $I^-$) are essentially equivalent. The examples which follow will show the preparation of such equivalent materials. This intermediate may be further reacted at this stage to introduce or change the $R_1$ and $R_2$ substituents. Particularly, sulfonate $R_1$'s or $R_2$'s may be introduced at this stage by liquid phase contact with 100% $H_2SO_4$ at 80°–150° C. for 0.5 to 2 hours, or by treatment with 15–30% oleum at room temperature (18° C.) to 50° C. for 0.5 to 5 hours.

The intermediate is next coupled to an amine. This may be a $$R_3\text{—}N\text{—}R_4$$
$$|$$
$$H$$

monomeric amine as has been defined or it may be an amine group-containing polymer backbone as has been described. In this step the amine displaces the halo leaving group on the anthraquinone ring as follows:

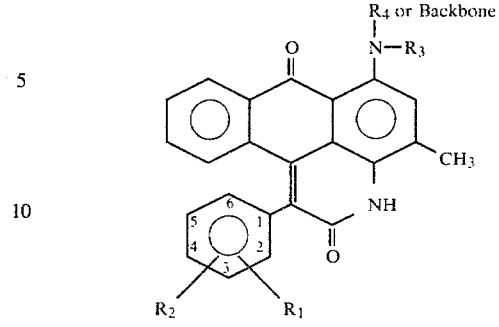

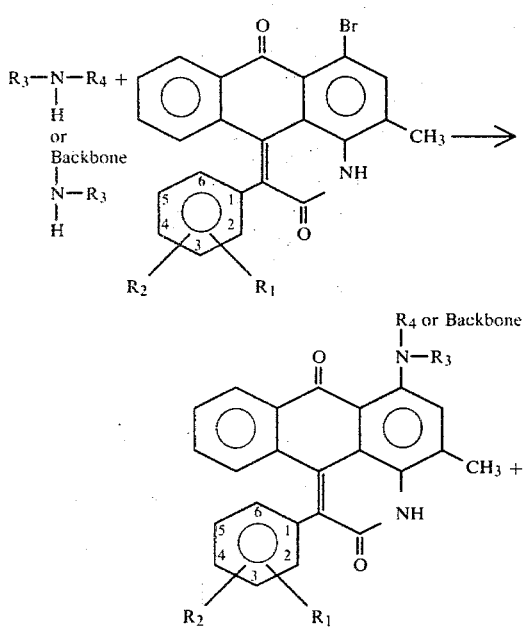

This step is carried out in liquid phase as well, generally in a water or mixed water/organic solvent and base and with a copper catalyst. This amine displacement is an adaption of the classic Ullmann reaction.

Water, and water containing up to about 25% of a water-miscible organic, such as an alkanol or glycol (methanol, ethanol, ethylene glycol and the like), mono and dialkyl ethers of ethylene glycols such as the materials marketed by Union Carbide under the trademark Cellosolve ®, and liquid organic bases such as pyridine may be used as solvent. Water and water containing up to about 20% pyridine are preferred solvents. The copper catalyst useful for this coupling may be copper metal, a copper (preferably cuprous) salt or an oxide of copper, for example finely divided copper metal, $Cu_2Cl_2$, and $Cu_2O$ supported on carbon black. A catalytically effective amount of catalyst is employed. Such an amount can range from about 0.01 to about 0.5 equivalents (preferably 0.05 to 0.4 equivalents) of copper per equivalent of reactive amine. Base, especially a strong inorganic base such as NaOH or KOH, should be present in an amount in excess of the molar amount of chromophore being coupled. Preferably from 0.5 to 5 equivalents (basis-free amine) of base is present with amounts from 1 to 3 (especially about 2) equivalents giving best results. The coupling is effected at a temperature of from about 60° C. to about 200° C., preferably 80° C. to about 150° C., and a time of from about 0.2 hours to about 24 hours, preferably 0.5 hours to about 8 hours, depending upon the temperature. This yields the coupled product as a crude reaction mixture. The desired product can be freed of catalyst and impurities as desired. It may also be subjected to post treatments such as acetylation or the like as desired.

The second preparative route is similar to the first. The acid chloride is attached to the AMBAX in the same way. Then, however, instead of separately cyclizing the AMBAX addition product, the uncyclized addition product is coupled to the amine or amine-containing backbone with the conditions of the coupling also effecting cyclization. Economies of production may favor the second route, but yields and product purities are often somewhat higher with the longer process.

The products of this invention are excellent red colors. Those containing polar groups in their chromophores or attached to their amines (i.e., when $R_4$ or the backbone contains a polar group) are water soluble. As solutions they present clear, bright intense reds. When added in coloring amounts such as from 10 to 10,000 ppm wt, they bond to and dye fibers and other substrates.

As polymeric dyes they present especially advantageous utilities as colorants for edibles. The polymer compounds wherein $R_1$ and $R_2$ are hydrogen are especially useful in this application as these materials are virtually a direct match in hue for now-banned Red #2. The other polymeric members of this colorant family are good reds for foods, blending well with yellows and blues to give the range of oranges, reds and grapes desired by the food industry.

For food use the colorants may be polymeric and of molecular weight above about 1000 Daltons, preferably above about 2000 Daltons so as to preclude their absorption through the walls of the G.I. tract.

In edible applications the polymeric colors are dissolved in beverages and syrups, dry mixed into powdered drink mix and cake mix, and otherwise conventionally admixed with foods, beverages, pharmaceuticals and cosmetics. The amount of color used in these applications will range between about 10 ppm wt and about 1000 ppm wt, basis finished food, beverage, or pharmaceutical. Cosmetic uses may require higher use levels.

The invention is further illustrated by the following examples. These are intended solely to exemplify the invention and are not to be construed as limiting the scope of the invention which is instead defined solely by the appended claims.

EXAMPLE I

Preparation of

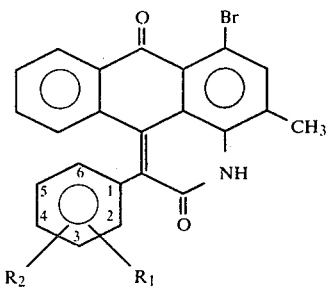

wherein $R_1$ and $R_2$ are hydrogen.

To the red slurry is added the phenylacetyl chloride and the mixture is heated to reflux. The reaction is followed by thin-layer chromatography. After one hour most of the starting material is gone. After three hours, the reaction appears to be over, although some starting material still remains.

After 3.5 hours total refluxing, the reaction is cooled to ca. 80° and filtered. The dark yellow filtrate is concentrated to ca. 30 ml on a rotary evaporator and cooled. A large amount of dark solid forms which is isolated and washed with ether until a yellow (dark) solid is obtained. The solid is oven dried at 70°, <1 mm, for four hours to afford 12.5 g (57.6%) of yellow-green solid product.

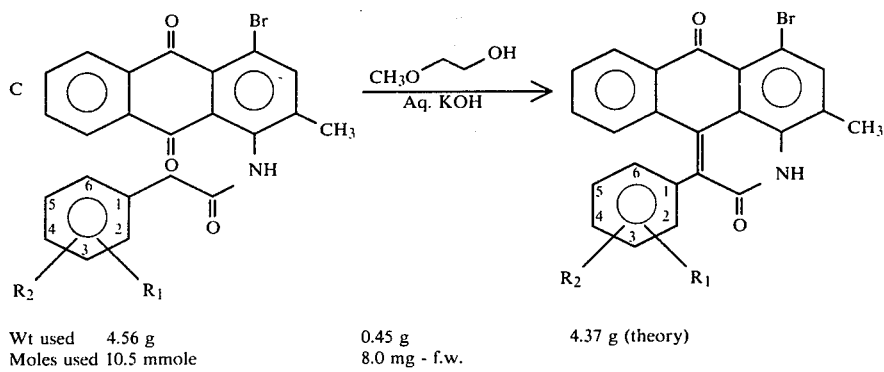

| Wt used 4.56 g | 0.45 g | 4.37 g (theory) |
| Moles used 10.5 mmole | 8.0 mg - f.w. | |

A. 1-amino-2-methylanthraquinone (300 g) is slurried with 1500 ml of HOAc in a 5-liter flask. The temperature is raised to 40° C. Neat bromine (405 g) is added over 2½ hours with stirring at 40°–50° C. The mixture is stirred for 20 additional minutes and filtered. The solids so recovered are washed with HOAc and water and sucked dry with an aspirator and transferred to a reaction flask along with 150 g of NaHSO₃ and 1.5 liters of water. The mixture is gradually heated to 90° C. (over two hours) with stirring to give 1-amino-2-methyl-4-bromoanthraquinone as a solid which is recovered from the reaction mixture by filtration in 90% yield, rinsed with water and dried overnight at 155° C. and 1 mm Hg absolute vacuum.

It will be appreciated that chlorine or iodine could be substituted for bromine in this reaction if desired.

A 100 ml 3-necked flask is equipped with water-cooled condenser, overhead stirrer, thermowell, and Ar inlet. The flask is charged with the phenylacetyl product of Part B, and 30 ml methyl cellosolve. The contents are heated to 122° and the KOH in 0.6 ml $H_2O$ is added dropwise over one minute. The reaction is stirred at 120° for one hour.

The reaction mixture is cooled to about 5° C. Isolation of a solid precipitate, followed by washing, affords 1.71 g (39.1%) of bright, shining gold solid.

The dark, yellow filtrate is concentrated via rotary evaporator to dryness and the dark solid is recrystallized from 170 ml of HOAc to afford 2.3 g (52.6%) of a dull, golden colored powder. Total yield is 4.01 g (91.8%).

EXAMPLE II

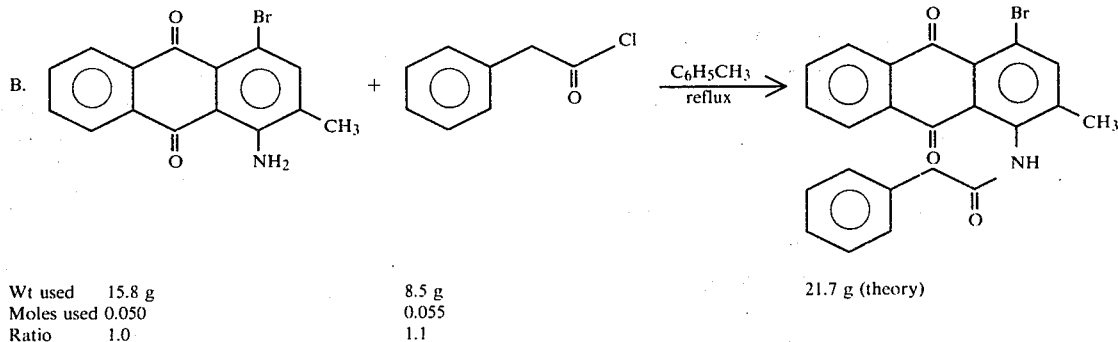

| Wt used 15.8 g | 8.5 g | 21.7 g (theory) |
| Moles used 0.050 | 0.055 | |
| Ratio 1.0 | 1.1 | |

A 250 ml flask equipped with overhead stirrer, water-cooled condenser, and Ar inlet is charged with the bromoanthraquinone of part A and 120 ml of toluene.

Preparation of a monomeric colorant from the product of Example I

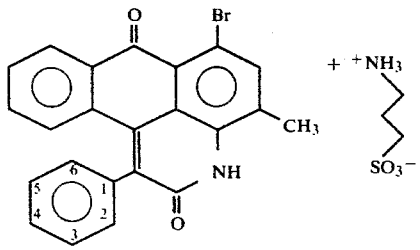 + $^+NH_3$ 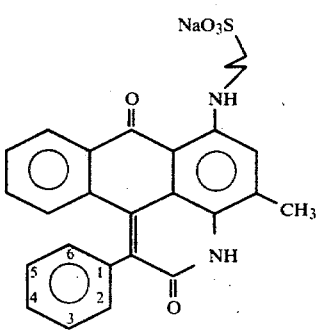 + Aqueous NaOH $\xrightarrow[\text{Cu}_2\text{Cl}_2]{\text{H}_2\text{O} \text{ pyridine}}$

| Wt used | 1.0 g | 0.306 g | 7.2 ml of 1N |
|---|---|---|---|
| Moles used | 2.4 mmole | 2.2 mmole | 7.2 mequiv. |

A 25 ml flask is charged with the product of Example I, sulfopropylamine, aqueous sodium hydroxide, 3.6 ml $H_2O$, 1.2 ml pyridine, and 40 mg cuprous chloride. The flask is equipped with a magnetic stirrer, thermowell, and reflux condenser. After flushing the system with argon and de-aerating, the contents are heated to reflux (95°–100°) for 3.3 hr. The reaction mixture is then cooled to room temperature, diluted with dilute sodium hydroxide solution, and carefully filtered to remove solids. The solution is then concentrated to dryness under reduced pressure, and the resultant solid dissolved back into water. The pure, monomeric dye can be isolated by preparative thin layer chromatography, preparative high pressure liquid chromatography, or by recrystallization.

EXAMPLE III

To 2304 g of acetamide (technical) in a 12 liter reaction flask is added 62.2 ml of 6 M aqueous sulfuric acid followed immediately by 661 g of acetaldehyde (99+%). This mixture is stirred and heated until the internal temperature reaches 78° C. (11 minutes) at which point the clear solution spontaneously crystallizes, causing a temperature rise to 95° C. The reaction product, ethylidene-bis-acetamide, is not separated. Heating and stirring are continued for another five minutes to a temperature of 107° C. and a mixture of 150 g calcium carbonate (precipitated chalk) and 150 g of Celite ® diatomaceous earth powder is added. A first distillate fraction of water and acetamide is removed. The remaining materials are cracked at 35 mm Hg and 185° C. A fraction made up of vinylacetamide and acetamide is taken overhead, analyzed by NMR and found to contain 720 g of vinylacetamide and 306 g of acetamide. A portion of this pooled material is dissolved in isopropanol, cooled, and filtered to yield a stock solution. This stock solution is analyzed and found to be 4.1 molar in vinylacetamide.

Into a five liter flask is added 505 ml (272 g) of a vinylacetamide solution obtained by stripping isopropanol from 900 ml of the above stock solution (containing 3.69 moles of vinylacetamide). AIBN (15 g) in 1500 ml of water is added followed by 1279 g of 25% W sodium vinylsulfonate in water (Research Organic Corporation) and a liter of water. This is two equivalents of sulfonate per three equivalents of vinylacetamide. Following deoxygenation, the mixture is heated to 65° C. and there maintained with stirring for three hours. This reaction mixture is then reduced to ⅓ volume, solid AIBN is removed and the liquid added to eight gallons of isopropanol. The copolymer precipitate is collected and dried in vacuum to yield 865 g of solid copolymer (MW $6.6\times10^4$). Whenever an experimental molecular weight is given in this specification, it is derived by gel permeation techniques. In the primary technique, a silanized porous glass support is used with a 0.01 M LiBr in DMF eluent. Detection is by refractometer with standardization being based on suitable purchased poly(styrene) or poly(styrene sulfonate) standards.

Into a two liter flask is added 863 g of the just-noted solid product, 2.5 liters of water and a liter of concentrated hydrochloric acid. The mixture is refluxed (99°–110° C.) for about 24 hours and cooled, and solid precipitate is washed, and dissolved in three liters of 10% NaOH. This mixture is added to about 12 liters of methanol to give 400 g of fine solid copolymer precipitate.

EXAMPLE IV

+ vinylamine-vinylsulfonate copolymer $\xrightarrow[\text{Cu}_2\text{Cl}_2, \text{NaOH}]{\text{H}_2\text{O/pyridine}}$ polymeric colorant.

| (Example I) | (Example III) | |
|---|---|---|
| Wt. used 0.958 g | 0.500 g | 0.077 g |
| Moles used 2.30 mmol | 3.835 meq | 0.39 mg - f.w. |
| Ratio 0.60 | 1.0 | 0.20 equiv. Cu⁺ |

A 50 ml two-necked flask is charged with the copolymer, 11.5 ml 1 N NaOH, 1 ml of pyridine and 4 ml H₂O. The system is de-aerated. The polymer dissolves and the anthraquinone and Cu₂Cl₂ are added and the mixture is heated to 97°. After 2½ hr, the mixture is cooled and diluted with 40 ml water at pH 11.

The diluted mixture is filtered to afford 100 ml of a red solution. The solution is ultrafiltered using 10% pyridine in water at pH 11 and later pH 7 water as makeup.

The red solution is lyophilized to afford 0.850 g of red solid which is determined to be

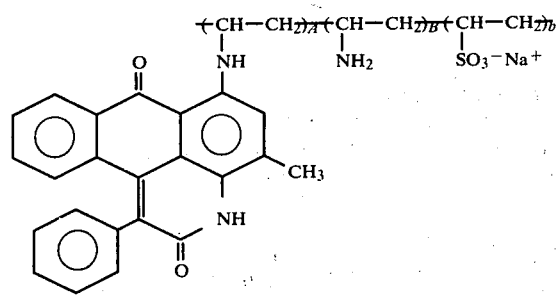

Wherein A+B+D equals about 900.
A = ~180
B = ~360
D = ~360.

EXAMPLE V

Preparation of an acetylated version of the colorant of Example IV.

The product of Example IV (255 mg) is dissolved in 12 ml of water and cooled to 5° C. Fifty percent NaOH is added to pH 12 followed by 0.2 g of acetic anhydride. The pH adjustment to 12 and acetic anhydride addition are repeated twice. The red solution is filtered, ultrafiltered and lyophilized to yield a solid product of Example IV wherein about 95% of the free backbone amines are converted to

groups. This red solid is an excellent colorant. It is very good replacement for existing red food colors. Virtually identical colors would result when the following changes are made.

1. The backbone amine to sulfonate ratio is varied from 1.5:1 to 2.0:1.
2. The backbone peak molecular weight is varied from 35,000 to 80,000.
3. The fraction of total backbone amines substituted with chromophores is varied from 25% to 40%.
4. The degree of acetylation is varied between 80% to 98% of the total amines.

EXAMPLE VI

Preparation of

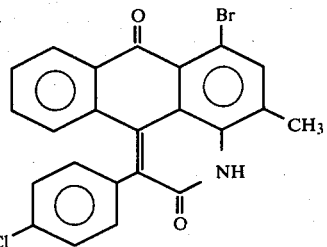

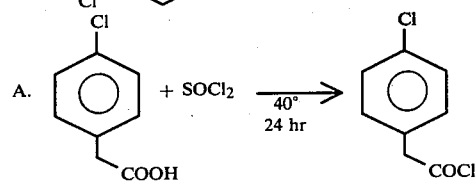

| | | | |
|---|---|---|---|
| Wt. used | 17.06 g | 11.90 g | 18.9 g (theory) |
| Moles used | 0.100 | 0.100 | |

A 50 ml flask is charged with the organic acid and the SOCl₂. A single boiling chip is added and the flask fitted with air condenser and drying tube. Heating in a 45° oil bath is begun. The reaction is cooled after 23 hours.

To the solution is added 5 ml of benzene. Volatile material is pumped off at room temperature at 0.5 mm Hg. The product is then distilled through a short path vacuum distillation apparatus as a water white product, b.p. 63°–64° at 0.10 mm Hg. The yield of distilled product is 12.3 g (65%).

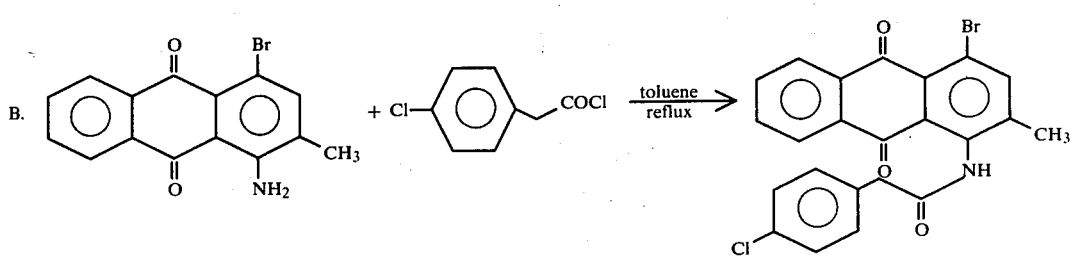

| | | | |
|---|---|---|---|
| Wt. used | 15.8 g | 10.87 g | 120 ml | 23.4 g (theory) |
| Moles used | 0.050 | 0.0575 | | |
| Ratio | 1.0 | 1.15 | | |

The procedure of Example II, Part B, is repeated using the above materials to afford the above product.

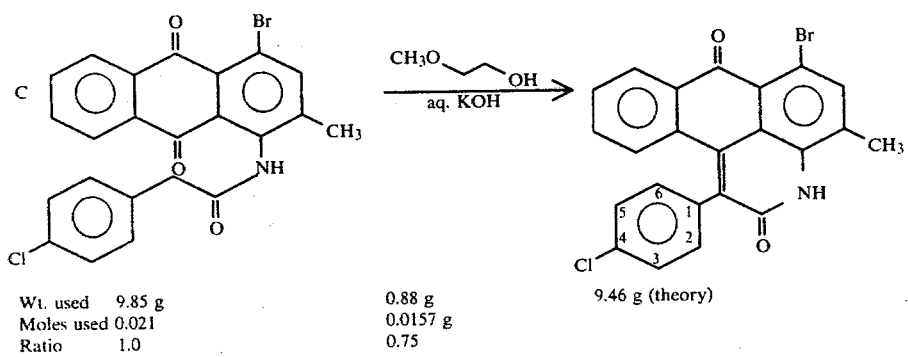

| | | |
|---|---|---|
| Wt. used 9.85 g | 0.88 g | 9.46 g (theory) |
| Moles used 0.021 | 0.0157 g | |
| Ratio 1.0 | 0.75 | |

The product of Part B and 60 ml of Cellosolve are added to a 250 ml flask. The slurry is heated to 123°. The KOH is dissolved in 1.0 ml H$_2$O and added over one minute. The reaction is cooled after heating at 115° for 35 minutes. The mixture is allowed to cool slowly to room temperature and then cooled to 5° C. A solid precipitate is isolated and washed to afford 3.32 g of glittering, brownish/golden crystals.

The dark filtrate is concentrated to dryness and the resultant dark solid recrystallized from 675 ml boiling HOAc. The greenish-yellow needles are isolated and washed. Drying at 85°, <1 mm for four hours affords 3.8 g of a golden solid.

EXAMPLE VII

If the preparation of Example VI is repeated using the chloro or iodo anthraquinones shown in Example I in place of the bromo anthraquinone, the corresponding chloro or iodo products would result.

Similarly, use of the 2,4-dichloro, the 2-chloro, the bromo or the iodo equivalents of the 4-chloro acid in place of the 4-chloro acid in step A of Example VI would result in the 2,4-dichloro, the 2-chloro, the bromo or the iodo-substituted products.

EXAMPLE VIII

Attachment of the product of Example VI to the polymer of Example III.

10% pyridine—pH 11 water. Then, the product is divided into two portions.

One portion is acetylated and the other is lyophilized to afford 490 mg of red solid in accord with Example V. The unacetylated product has the formula

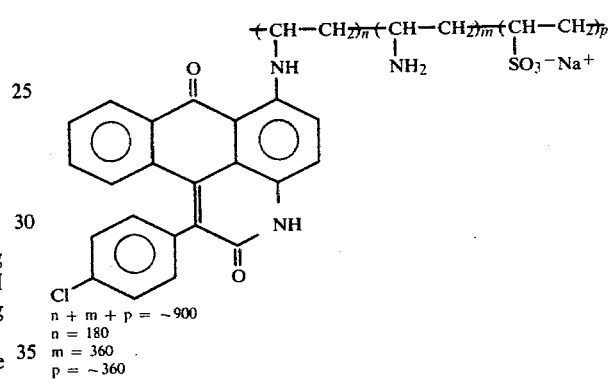

$n + m + p = \sim 900$
$n = 180$
$m = 360$
$p = \sim 360$

The acetylated version differs only in that the residual NH$_2$'s on the backbone are present as NHAc's. Both are excellent red colorants.

Substitution of the products of Example VII for the product of Example VI as feedstock for this Example would yield their polymer product counterparts.

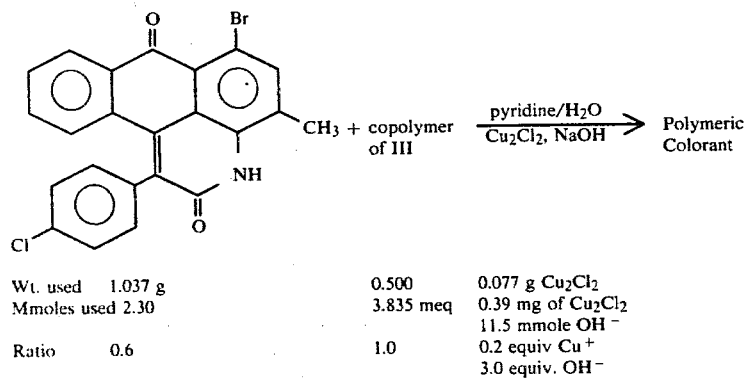

| | | |
|---|---|---|
| Wt. used 1.037 g | 0.500 | 0.077 g Cu$_2$Cl$_2$ |
| Mmoles used 2.30 | 3.835 meq | 0.39 mg of Cu$_2$Cl$_2$ |
| | | 11.5 mmole OH$^-$ |
| Ratio 0.6 | 1.0 | 0.2 equiv Cu$^+$ |
| | | 3.0 equiv. OH$^-$ |

The copolymer is dissolved in 11.5 ml 1 N NaOH and 4 ml H$_2$O. The solution is de-aerated (3 times, with Ar) and the anthrapyridone derivative, Cu$_2$Cl$_2$, and pyridine (1.5 ml) are added. The reaction is stirred at 96°–97° for two hours and 40 minutes, then cooled and diluted with dilute aqueous sodium hydroxide.

The dilute mixture is filtered to afford 115 ml of a dark red dye solution. Ultrafiltration is carried out with

EXAMPLE IX

Preparation of

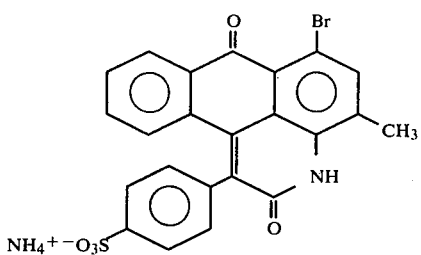

The product of Example I,

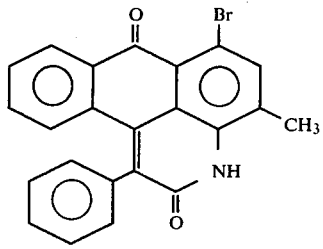

0.6 g and 4.4 g of 20% oleum are stirred together at room temperature. After one-half hour, it appears that reaction has occurred. The stirring is continued for a total of five hours. The reaction mixture is poured over ice and water and a solid precipitate forms and is collected. The solid is dissolved in a liter of 2 M $NH_4OH$, filtered and the solution is evaporated to dryness. The solid which results is extracted with methanol. The methanol is evaporated to afford 0.775 g of the desired sulfonate product.

EXAMPLE X

Formation of a homopolymeric polyaminoethylene backbone for coupling colors into polymeric form.

A red-brown solution of 460 g of vinylacetamide, 557 g acetamide, and 123 g ethylidene-bis-acetamide, (one-half of five combined vinylacetamide preparations essentially in accord with Example III) in 570 ml methanol is filtered through 250 g of Amberlite ® IRC-50 ion exchange resin over an eight-hour period. The column is rinsed with 1000 ml methanol. The combined column eluent is stripped to its original volume of 1,667 ml, treated with 7.75 g of AIBN polymerization catalyst (1 mole %), deoxygenated, and stirred under Argon at 65° C. for 15 hours to polymerize. Solid polymer is precipitated from the resulting very thick solution by addition to 15 liters of acetone. The polymer is collected by filtration, washed with acetone and dried in a vacuum oven (80° C.) for two days to afford 459 g of crude poly(vinylacetamide) contaminated with acetamide as a yellow, semigranular solid having molecular weight of $2 \times 10^4$ as determined by Gel Permeation Chromatography, using dimethylformamide as eluent and polystyrene as standards.

The crude poly(vinylacetamide) (459 g) is dissolved in 1000 ml water with heating. Concentrated hydrochloric acid (1000 ml) is added and the resulting dark brown solution is stirred and heated at a gentle reflux (97°–106° C.) for 19 hours. A precipitate forms and is redissolved by addition of 200 ml water. Reflux is continued and over the next eight hours 1000 ml water is added in several portions to maintain solubility of the polymer. After a total of 27 hours at reflux, the polymer is precipitated by the addition of 1000 ml concentrated hydrochloric acid. The mixture is cooled to 18° C. and the thick polymeric gum isolated by decantation and dried under vacuum at 50°–75° C. with occasional pulverization for 40 hours to give 332 g of poly(vinylamine hydrochloride) as a brown granular solid (77% yield from vinylacetamide, 59% from acetaldehyde).

EXAMPLE XI

Formation of a polymeric colorant from the anthraquinone product of Example IX and the polymer product of Example X.

Following the procedures of Examples IV, 0.754 g of the anthraquinone product of Example IX is coupled to 0.200 g of the polyaminoethylene product of Example X. Copper catalyst (0.021 g) and NaOH (three equivalents basis polymer) are used. The reaction is carried out for one hour at 97° C. The reaction mixture is diluted and filtered and ultrafiltered. The retentate of the ultrafiltration is divided into two portions. One is lyophilized to afford the following product

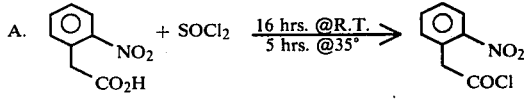

$m \cong 260$
$n \cong 200$

The other portion is acetylated in accord with the general procedure of Example V to give a product wherein the residual backbone amines are acetylated. In this and in all acetylations in this disclosure, conversion of amines to amides is usually not quantitative. Usual conversions are 80–98% of the amine being converted.

EXAMPLE XII

A.

| | | |
|---|---|---|
| Wt. Used | 18.11 g | 12.0 | 19.9 (theory) |
| Moles Used | 0.100 | 0.101 | |

The reagents are weighed into a flask and allowed to stand at room temperature (~21°) overnight. A stirring bar is added and the reaction driven to completion by warming at 35° until no solid is visible (five additional hours). To the red solution is added 5 mls benzene and the volatile material is removed with vacuum.

B. The 2-nitro acid chloride of Part A is reacted with AMBAX and the ring is closed to give the product

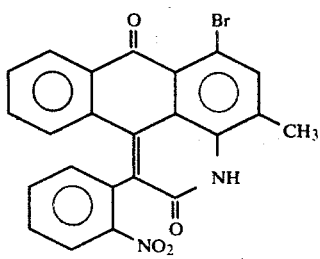

The general reactions of Example I are used. The reaction of this acid chloride with AMBAX is more facile and requires only three hours at reflux.

C. The product of Part B is attached to the polymer of Example III using the method of Example IV. This product is divided into two portions, one of which is acetylated.

EXAMPLE XIII

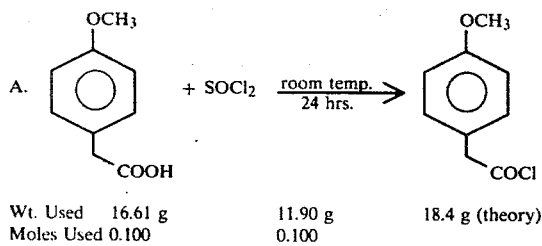

| Wt. Used | 16.61 g | 11.90 g | 18.4 g (theory) |
|---|---|---|---|
| Moles Used | 0.100 | 0.100 | |

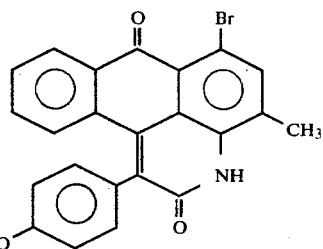

A flask is charged with the carboxylic acid and thionyl chloride and allowed to stand at room temperature with occasional swirling for 24 hours. The endothermic reaction begins immediately and proceeds at a very good rate, generating an orange solution.

After 24 hours, nearly all gas evolution has ceased. Six ml benzene is added and the volatile material is removed with vacuum. The product is purified by distillation.

B. A flask is charged with 15.8 g AMBAX and 115 ml toluene. Then, the acid chloride, 10:1 g, is added. The red slurry is heated to reflux for 2.0 hours.

The hot mixture is filtered and a black residue washed with three portions of hot toluene. The toluene is stripped off affording a solid which is washed with ether. The product is dried overnight at 70°, <1 mm to afford 19.48 g of dull green powder.

This product is treated with base in accord with the procedures of Example 1, Part C, to yield

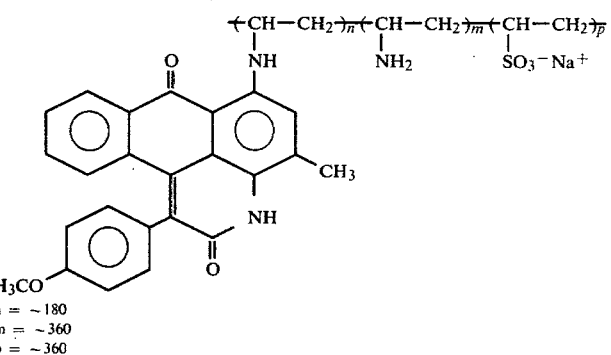

C. The product of Part B is coupled to the polymer of Example III to afford a polymeric dye of the structure

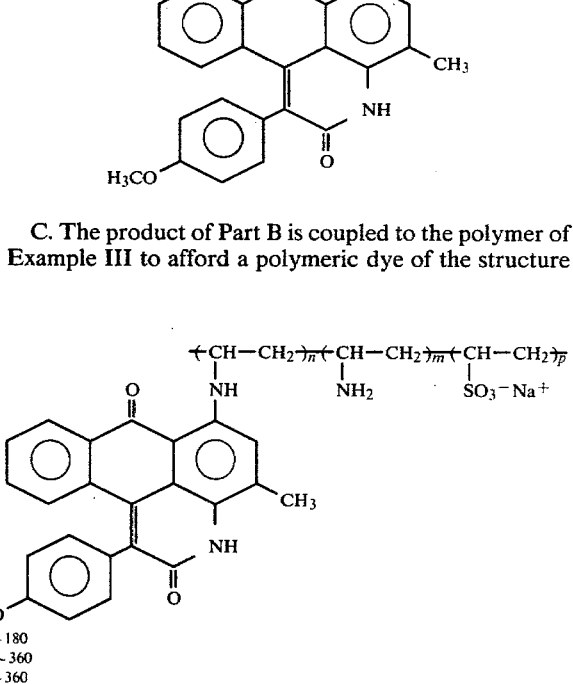

n = ~180
m = ~360
p = ~360

EXAMPLE XIV

This example illustrates an alterative preparation of the compound of this invention.

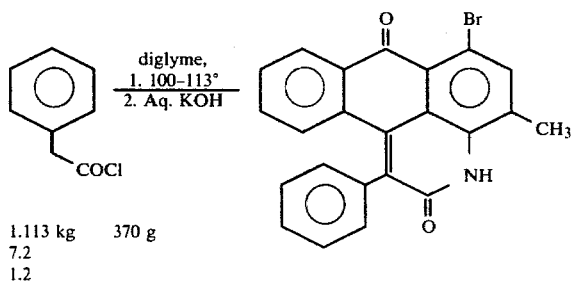

| Wt. used | 1.897 kg | 1.113 kg | 370 g |
|---|---|---|---|
| Moles used | 6.0 | 7.2 | |
| Ratio | 1.0 | 1.2 | |

A 22-liter resin kettle is charged with the anthraquinone and 13.8 liter of diglyme. The reactor is fitted with a 4-necked head which is equipped with overhead stirrer, thermocouple, argon outlet/reflux condenser, and an argon inlet to sweep the system. The reaction mixture is then heated to 111°-113° and the acid chloride is added quickly. After 30 minutes at 111°-113°, a pH probe is inserted into the reaction mixture in place of the argon inlet. A solution of 370 g of potassium hydroxide in 346 ml of water is then carefully added portionwise while the pH of the system is monitored. By the end of the hydroxide addition, the pH meter should give a reading of ca. 10.3. Product soon begins to drop out and after a total reaction time of 90 minutes (including 30 minute acetylation time) the heating mantle is turned off.

Next the system is cooled refluxively by gradually reducing the internal pressure using a water aspirator. When the pressure reaches 27-inch Hg of vacuum, the internal temperature is 55°. The vacuum is released and 3 liter of methanol are added. The resultant slurry is then filtered via a ceramic filtering crock and sucked dry. The filter cake is washed with one 4-liter portion of methanol, sucked dry at a large water aspirator, and finally vacuum oven dried overnight at 80°, 0.4 mm Hg. The yield of yellow-green product is 1.904 kg (76%).

EXAMPLE XV

This example shows a one-step closing and attachment to a backbone.

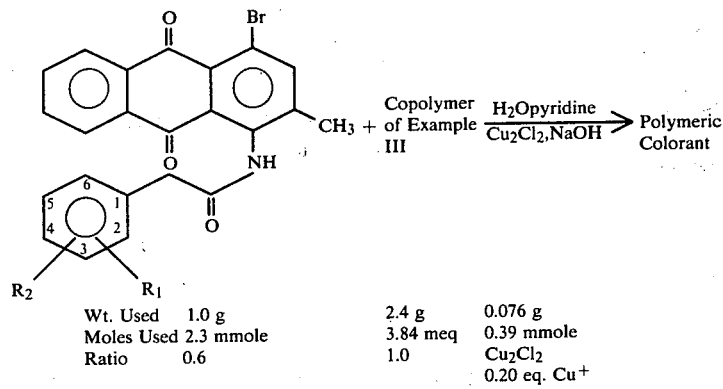

Wt. Used    1.0 g         2.4 g       0.076 g
Moles Used  2.3 mmole     3.84 meq    0.39 mmole
Ratio       0.6           1.0         $Cu_2Cl_2$
                                      0.20 eq. $Cu^+$ A 25 ml flask is charged with the anthraquinone derivative, the copolymer backbone, 11.5 mls 1 N NaOH solution, 1.3 mls pyridine, and the cuprous chloride. The flask is equipped with reflux condenser, magnetic stirrer, and thermocouple. The system is then deaerated and flushed with argon. The reaction mixture next is stirred and heated at 96°–100° C. for 3.5 hours, after which time the reaction mixture is cooled, diluted, filtered, and ultrafiltered. The resultant dye is then acetylated as in Example V and worked up as in Example V to afford a red dye which is indistinguishable from the dye prepared according to Example V.

What is claimed is:
1. A compound of the formula

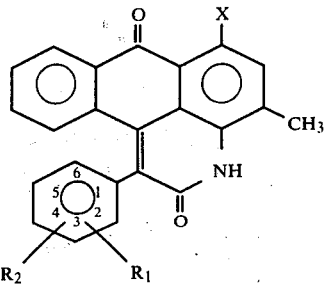

wherein $R_1$ and $R_2$ are independently selected from the group of hydrogen, halos of atomic number 9 through 53 inclusive, lower alkyls and lower alkoxies of from 1 to 3 carbon atoms, nitros, and sulfonates and wherein X is a halo of atomic number 17 through 53 inclusive.

2. The compound of claim 1 wherein $R_1$ is hydrogen.
3. The compound of claim 2 wherein $R_2$ is hydrogen.
4. The compound of claim 3 wherein X is bromo.
5. The compound of claim 2 wherein $R_2$ is a halo of atomic number 9 through 53 inclusive and $R_2$ is in the 2 or 4 position.
6. The compound of claim 5 wherein $R_2$ is chloro and X is bromo.
7. The compound of claim 2 wherein $R_2$ is a lower alkoxy of from 1 to 3 carbon atoms and $R_2$ is in the 2 or 4 position.
8. The compound of claim 7 wherein $R_2$ is methoxy and X is bromo.
9. The compound of claim 2 wherein $R_2$ is sulfonate and $R_2$ is in the 4 position.
10. The compound of claim 2 wherein $R_2$ is nitro and $R_2$ is in the 2 or 4 position.
11. The compound of claim 2 wherein $R_2$ is a lower alkyl of 1 to 3 carbon atoms and $R_2$ is in the 2 or 4 position.

* * * * *